(12) United States Patent
Plana-Duran et al.

(10) Patent No.: US 8,067,013 B2
(45) Date of Patent: Nov. 29, 2011

(54) MULTIVALENT AVIAN INFLUENZA VACCINES

(75) Inventors: Juan Plana-Duran, Santa Pau (ES); Rut Vila-Quintana, Olot (ES); Jordi Tarres-Call, Banyoles (ES); Mahesh Kumar, Fort Dodge, IA (US)

(73) Assignee: Wyeth LLC, Madison, NJ (US)

( * ) Notice: Subject to any disclaimer, the term of this patent is extended or adjusted under 35 U.S.C. 154(b) by 1506 days.

(21) Appl. No.: 11/244,574

(22) Filed: Oct. 6, 2005

(65) Prior Publication Data

US 2006/0204976 A1 Sep. 14, 2006

Related U.S. Application Data

(60) Provisional application No. 60/616,707, filed on Oct. 7, 2004, provisional application No. 60/648,459, filed on Jan. 31, 2005.

(51) Int. Cl.
*A61K 39/145* (2006.01)
*A61K 39/295* (2006.01)
(52) U.S. Cl. ............... 424/209.1; 424/204.1; 424/210.1
(58) Field of Classification Search ........................ None
See application file for complete search history.

(56) References Cited

FOREIGN PATENT DOCUMENTS

EP 0399843 A 11/1990
WO WO 03/086453 10/2003

OTHER PUBLICATIONS

Donatelli, et al., 2001 J Gen Virol 2001 vol. 82, pp. 623-630.*
Fatunmbe et al. Avian pathology 1992 vol. 21 pp. 225-237.*
Capua et al. Avian pathology 2002 vol. 32 pp. 47-55.*
Avian Pathology, vol. 33(4), pp. 393-404, Aug. 2004, Avian Influenza: Recent Developments, Ilaria Capua, et al.
Journal Of Virology, vol. 73(7), pp. 5903-5911, Jul. 1999, A Mouse Model For The Evaluation Of Pathogenesis And Immunity To Influenza A (H5N1) Viruses Isolated From Humans, Xiuhua Lu, et al.
Avian Diseases, vol. 42(2), pp. 248-256, Apr. 1998, Efficacy Of Inactivated H5N2 Influenza Vaccines Against Lethal A/Chicken/Queretaro/19/95 Infection, Alejandro Garcia, et al.
Avian Pathology, vol. 21(2), pp. 225-237, 1992, Efficacy Of Avridine And Liposomes As Adjuvants For Avian Influenza Virus Antigens In Turkeys, O. O. Fatunmbi, et al.
Avian Pathology, vol. 28(3), pp. 245-255, Jun. 1999, Influence Of Virus Strain And Antigen Mass On Efficacy Of H5 Avian Influenza Inactivated Vaccines, Huntingdon, Cambs, GB, D. E. Swayne, et al.
André, F.E., "Development of Combined Vaccines: Manufacturers' Viewpoint," Biologicals 22:317-321 (1994).
Capua et al., "Developments of a DIVA (Differentiating Infected from Vaccinated Animals) Strategy Using a Vaccine Containing a Herterologous Neuraminidase for the Control of Avian Influenza;" Avian Pathology 32, 47-55 (2002).
Cattoli, et al. "Comparison of three rapid detection systems for type A influenza virus on tracheal swabs of experimentally and naturally infected birds," Avian Pathology, 33(4), pp. 432-437. (2004).
Clemens, J., et al., "Interactions between PRP-T Vaccine against *Hemophilus influenzae* Type b and Conventional Infant Vaccines Lessons for Future Studies of Simultaneous Immunization and Combined Vaccines," In: Combined Vaccines and Simultaneous Administration. Current Issues and Perspectives (Eds. Williams, J.C., et al.) The New York Academy of Sciences, New York, pp. 255-266 (1995).
Ellis, et al., "Vaccination of Chickens Against H5N1 Avian Influenza in the Face of an Outbreak Interrupts Virus Transmission," Avian Pathology 55(4), pp. 405-412 (Aug. 2004).
Goldenthal, K, L., et al., "Overview—Combination Vaccines and Simultaneous Administration. Past, Present, and Future," In: Combined Vaccines and Simultaneous Administration, Current Issues and Perspectives (Eds. Williams, J.C., et al.) The New York Academy of Sciences, New York, pp. 1 XI-XV (1995).
Hadler, S.C., "Cost benefit of combining antigens," Biologicals 22:415-418 (1994).
Insel, R.A., "Potential Alterations in Immunogenicity by Combining or Simultaneously Administering Vaccine Component," In: Combined Vaccines and Simultaneous Administration. Current Issues and Perspectives (Eds. Williams. J.C., et al.) The New York Academy of Sciences, New York, pp. 35-47 (1995)).

* cited by examiner

*Primary Examiner* — Mary E Mosher
*Assistant Examiner* — Myron Hill
(74) *Attorney, Agent, or Firm* — Michael J. Moran; Kelly M. Sullivan

(57) ABSTRACT

A vaccine composition and method which is effective in preventing or ameliorating Avian Influenza Virus infection is set forth herein. The vaccine contains at least two inactivated strains of avian influenza virus, wherein the combined haemoagglutinin (HA) total is at least about 200 HA/dose of the vaccine composition, and wherein each of the strains presents at least about 128 HA/dose, and further wherein one of the strains has the same HA subtype as that of a challenge virus, and wherein at least one of the strains has a different NA subtype than the challenge virus.

17 Claims, No Drawings

MULTIVALENT AVIAN INFLUENZA VACCINES

CROSS-REFERENCE TO RELATED APPLICATIONS

This application claims the benefit of U.S. provisional patent application Nos. 60/616,707, filed on Oct. 7, 2004, and 60/648,459, filed on Jan. 31, 2005.

FIELD OF THE INVENTION

The present invention relates to novel multivalent avian influenza vaccines useful for vaccinating susceptible avians in the face of an outbreak of disease. The invention also relates to new methods for preventing or ameliorating avian influenza viral disease in poultry.

BACKGROUND OF THE INVENTION

Avian Influenza, also called "AI," is an acute and highly contagious viral infection of chickens and other fowl. As an influenza virus, it is classified in subtypes on the basis of antigen differences in the haemoagglutinin (HA; also may be abbreviated as H) and neuroaminidase (NA; also may be abbreviated as N) molecules, which "reassort" or "mutate" from season to season. Because it constantly mutates, vaccine preparation is difficult due to the unpredictability as to which strain will reappear in subsequent seasons. The strains used for vaccine preparation often do not reproduce under manufacturing conditions at a very fast rate, so that waiting for an appearance of a particular strain, and then manufacturing the correct vaccine to protect against the strain does not provide a viable option. Typically, the epidemic of the particular strain will last for several months, and then perhaps disappear for several years.

Eradication is the principal method for controlling the disease in avians, without obvious economic disadvantages, but if a vaccine with a fast onset of immunity could be produced, such a product would offer a viable alternative to mass slaughter of entire flocks.

The influenza viruses are known to be classifiable in the various A, B. C topologies, according to the group antigen the viruses carry. The influenza viruses of the A, B. C types can be distinguished from one another on the basis of the antigen differences that can be found in the viral nucleocapsid (NP) and matrix (M) proteins. In particular, the A-type influenza viruses can be classified into subtypes on the basis of antigen differences in the haemoagglutinin (HA) and neuroaminidase (NA) molecules. Presently nine subtypes of the neuroaminidase NA proteins, designated NA1 to NA 9, and fifteen different subtypes of the serum haemoagglutinin HA proteins, designated HA 1 to HA 15, have been identified. In birds, viruses carrying any of the various HA (or H) and NA (or N) subtypes have been isolated.

HA is a viral surface glycoprotein comprising approximately 560 amino acids and representing 25 of the total virus protein. It is chiefly responsible of adhesion of the viral particle to the host cell and of 25 its penetration into the latter in the early stages of the infection. Haemoagglutinin, among the viral proteins, is the one that is most subject to post-translational rearrangements. After the synthesis thereof has been completed, the molecule follows the 5 exocytotic pathway of the host cell, in the course of which HA is folded, assembled in trimers and glycosylated. Finally it is cleaved into two subunits H1 and H2; this cleavage is the key step in the activation of the molecule and in the acquisition of 10 the infective capacity by the virion.

It is well known, in fact, that the different composition of the cleavage site, concerning the basic amino acid residues, translates into the capacity of the avian influenza virus to produce localized, or symptomatic infections, or, vice versa, generalized infections having a lethal outcome for many avian species. It has therefore been suggested that this fact might influenza the organ-tropism, the host specificity, as well as the pathogenicity of the virus. With respect to the pathogenicity of the virus, strains with multibase-site HA find proteases that cleave the HO molecule, in the active form Hi and H2 in several cellular types thus giving rise to multiple infection cycles with a massive production of 25 infectious viral particles and causing a generalization of the infections in all of the districts within a short time period (HPAI strains). The infection will consequently turn out to have an acute-hyperacute course, with very high mortality.

Neuroaminidase (NA) represents the second membrane glycoprotein of the influenza A viruses. it is coded for by a gene (segment 6 of the virus RNA) of 1413 nucleotide length that codes for a 413 amino acid peptide. This protein has at least two important 10 functions: destruction of the cellular receptor for the viral haemoagglutinin by cleaving between the sialic acid molecule and the haemoagglutinin itself. In this way it is supposed to possibly ease the liberation of the viral progeny by preventing the newly formed viral particles from accumulating along the cell membrane, as well as promoting the transportation of the virus through the mucus that is present on the mucosal surface. NA moreover represents an important antigen determinant that is subject to antigenic variations.

There currently exists a need in the art for avian influenza vaccines which would provide a useful alternative to eradication of infected flocks. Such vaccines would need to elicit a quick immune response in the vaccinated avian, and preferably would enable vaccinated birds to be able to be differentiated from infected birds. Bivalent or polyvalent influenza vaccines have been postulated to be utilizable in the so-called "DIVA" methods, where a vaccine is administered having an N different from the strain being vaccinated against so as to provide a means of differentiating vaccinated from infected birds. Published PCT WO 03/086453, whose disclosure is incorporated in its entirety by reference, describes the DIVA technology, and some representative vaccines utilizable in the methods thereof.

Combined or multivalent vaccines offer a number of obvious advantages over monovalent vaccines. One advantage of a multivalent vaccine is that fewer vaccine inoculations are required. A single preparation can be administered in one inoculation and is effective against several diseases or strains of a single disease. As the range of potential viral strains increases, the combination of vaccines becomes even more mandatory in order to minimize the number of inoculations. The decreased number of inoculations needed when vaccines are combined would likely lead to an increased compliance to the vaccination schedule. This in turn would likely lead to a resulting increase in vaccine coverage, which would ultimately lead to better disease control.

An unexpected problem of combined vaccines is the recently identified negative influence that one vaccine may have on another in a combination vaccine, the so-called "antigen interference" effect. It has been found that when two existing vaccines are simply mixed, one or both may lose their potency (Andre, F. E., "Development of Combined Vaccines: Manufacturers' Viewpoint," Biologicals 22:317-321 (1994); Hadler, S. C., "Cost benefit of combining antigens," Biologicals 22:415-418 (1994); Goldenthal. K, L., et al., "Overview—Combination Vaccines and Simultaneous Administration. Past, Present, and Future." In: *Combined Vaccines and Simultaneous Administration, Current Issues and Perspectives* (Eds. Williams, J. C., et al.) The New York Academy of Sciences, New York, pp. 1 XI-XV (1995); Clemens, J., et al., "Interactions between PRP-T Vaccine against *Hemophilus influenzae* Type b and Conventional Infant Vaccines Lessons for Future Studies of Simultaneous Immunization and Combined Vaccines." In: *Combined Vaccines and Simultaneous Administration. Current Issues and Perspectives* (Eds. Williams, J. C., et al.) The New York Academy of Sciences, New York, pp. 255-266 (1995); Insel, R. A., "Potential Alterations in Immunogenicity by Combining or Simultaneously Administering Vaccine Component,". In: *Combined Vaccines and Simultaneous Administration. Current Issues and Perspectives* (Eds. Williams. J. C., et al.) The New York Academy of Sciences, New York, pp. 35-47 (1995)).

Unfortunately, it cannot always be predicted by the use of currently established potency tests in the laboratory whether individual vaccine components will retain their potency. For example, several independent studies reported that when the Hib vaccine is combined with a whole cell pertussis vaccine there is no interference between the two vaccines but when the Hib vaccine is combined with acellular pertussis vaccines there is a substantial loss of the Hib immunogenicity. It was shown that when Hib is combined with DTaP, it maintains its immunogenicity if given at separate sites, while the immunogenicity is 5-15 times lower when the vaccines administered combined at the same site. This unexpected result confirms that combining two existing vaccines may not be a simple or routine process, and such combination often gives very unpredictable results that are not detected during the initial studies. The studies required to document non-interference often adds several additional months or years of studies to document non-interference, and suitability for use.

Bivalent avian influenza vaccines have been available in the marketplace, such as the vaccine known as Fluvac® marketed by Merial, but there still exists a need for improved bivalent or polyvalent avian influenza vaccines which invoke a rapid immune response, and a higher titre response, and which can thus be utilized to quickly protect birds in the face of an outbreak.

SUMMARY OF THE INVENTION

In one aspect, the invention is directed to a vaccine composition which is effective in preventing or ameliorating avian influenza, and which can be utilized in DIVA technology, and which further has the advantages of providing a rapid onset of immune response, which comprises an HA/dose rate of greater than about 200 HA/dose, and most preferably, in the range of about 250-300 HA/dose.

Thus, the invention provides a vaccine composition comprising at least two strains of avian influenza wherein the combined HA/dose is greater than about 200 HA/dose, and preferably is about 250-300 HA/dose. The amount of the HA/dose of each of the avian influenza strains may vary, but is typically at least about 75 HA/dose, and most preferably is greater than about 128 HA/dose.

The particular avian influenza strains chosen for the bivalent or multivalent vaccine of the present invention are dependent upon the particular strain prevalent in the are where the vaccine is to be administered. Most preferably, one of the strains with have a HA subtype identical to the HA subtype of the prevalent or challenge strain, and a differing N component so as to enable use of the DIVA technology. The additional strains may be selected from other HA subtypes having an incidence in the area to be treated, again preferably with differing N subtype.

As a further part of the invention there is provided a vaccine composition which is effective in preventing or ameliorating Avian Influenza Virus infection, which comprises at least two inactivated strains of avian influenza virus, wherein the combined haemoagglutinin (HA) total is at least about 200 HA/dose of the vaccine composition, and wherein each of the strains presents at least about 128 HA/dose, and further wherein one of the strains has the same HA subtype as that of a challenge virus, and wherein at least one of the strains has a different NA subtype than the challenge virus.

Also provided herein is a method of preventing or ameliorating an outbreak of Avian Influenza virus infection, which comprises administering to a poultry member a vaccine composition which contains at least two inactivated strains of avian influenza virus, wherein the combined haemoagglutinin (HA) total is at least about 200 HA/dose of the vaccine composition, and wherein each of the strains presents at least about 128 HA/dose, and further wherein one of the strains has the same HA subtype as that of a challenge virus, and wherein at least one of the strains has a different NA subtype than the challenge virus.

There is also provided a vaccine composition which is effective in preventing or ameliorating Avian Influenza Virus infection, which comprises at least two inactivated strains of avian influenza virus, wherein the combined haemoagglutinin (HA) total is at least about 250 HA/dose of the vaccine composition, and wherein each of the strains presents at least about 150 HA/dose, and further wherein one of the strains has the same HA subtype as that of a challenge virus, and wherein at least one of the strains has a different NA subtype than the challenge virus, and also wherein the composition contains two surfactants consisting essentially of sorbitan oleate esters.

These and other embodiments, features and advantages of the invention will become apparent from the detailed description and the appended claims set forth herein below.

DETAILED DESCRIPTION OF THE INVENTION

In one aspect, the present invention is directed to novel polyvalent avian influenza vaccines having a total HA content of greater than about 200 HA/dose.

The avian influenza isolates useful for the vaccines of the present invention may be isolated using techniques available in the art. For example, tissue or serum from infected chickens may be obtained from a commercial broiler flock. The virus may then be passaged in tissue or other suitable media to establish a master seed virus. Further characterization by the skilled artisan may also be undertaken using available methods. The viruses may be inactivated using available methods, such as heat and chemical treatment, for example.

In a further aspect herein, the invention also comprises a vaccine composition containing at least two avian influenza strains.

The vaccine composition of the invention may be formulated using available techniques, preferably with a pharmacologically acceptable carrier. For example, in one embodiment an aqueous formulation is contemplated. Such formulations utilize water, saline, or phosphate or other suitable buffers. In still another embodiment, the vaccine composition is preferably a water-in-oil or oil-in-water emulsion. Also contemplated are double emulsions, often characterized as water-in-oil-in-water emulsions. The oil may help to stabilize the formulation and further function as an adjuvant or enhancer. Suitable oils include, without limitation, white oil, Drakeoil, squalane or squalene, as well as other animal, vegetable or mineral oils, whether naturally-derived or synthetic in origin.

In addition, the vaccine composition may contain other suitable adjuvants available in the art. These can include aluminum hydroxide and aluminum phosphate, for example, as well as other metal salts.

Additional excipients may also be included in the vaccine composition, such as surfactants or other wetting agents or formulation aids. Surfactants can include the sorbitan monooleate esters (TWEEN® series), as well as the ethylene oxide/propylene oxide block copolymers (PLURONIC® series), as well as others available in the art. Other compounds recognized as stabilizers or preservatives may also be included in the vaccine. These compounds include, without limitation, carbohydrates such as sorbitol, mannitol, starch, sucrose, dextrin or glucose and the like, as well the preservative formalin, for example.

The vaccine composition may also be formulated as a dry powder, substantially free of exogenous water, which may then be reconstituted by an end user prior to administration.

The vaccine composition is most preferably formulated utilizing killed or inactivated virus. Also contemplated for use herein is a recombinant vaccine, which expresses the required HA proteins at the necessary level so as to provide a total HA content of greater than about 200.

The vaccine composition of the invention will preferably contain a minimum of about 200 HA total from its influenza viral components. In one embodiment of the invention, the vaccine will contain about 128 HA/dose from each strain, and even more preferably about 192 HA/dose from each strain.

Other poultry antigens against other diseases may also be included and administered with the vaccine composition of the invention. For example, vaccine antigens against chicken herpes virus, chicken anemia virus (CAV), Newcastle Disease virus and Infectious Bronchitis (IB) virus, as well as reovirus antigens may be included as part of the vaccine composition of the invention. One or more reovirus antigens may be particularly preferred as part of the vaccine composition of the invention.

The invention is also directed to a method for inducing protection against infection from avian influenza virus. The method involves administering to a poultry animal a vaccine composition containing at least two strains of avian influenza virus with the combined HA content of greater than about 200 HA/dose, with 250 to 300 HA/dose being particularly preferred.

The method of administration may be selected by the skilled artisan. For instance, the vaccine composition may be administered to post-hatch, young (few days to several weeks old) chicks via drinking water, spraying or eye drops. In ovo administration is contemplated herein. For example, embryos may be inoculated, usually at about day 18-19. Other methods wherein the vaccine composition of the invention is administered parenterally, subcutaneously, peritoneally, orally, intranasally, or by other available means, preferably parenterally, more preferably intramuscularly, in effective amounts according to a schedule which may be determined according to the time of anticipated potential exposure to a carrier of the disease-causing Avian Influenza Virus, are also within the scope of the invention.

A dose is typically within the range of about 0.25 mL to about 2.0 mL per poultry animal, more preferably about 0.5 mL to about 1.0 mL per animal. Thus, one, two or more doses are contemplated herein, with as few as possible being particularly preferred.

As set forth above, the invention is directed to novel avian influenza vaccine compositions and methods for use thereof poultry. The term "poultry" is intended to encompass, without limitation, all commercially-bred poultry animals, including chickens, ducks, geese, turkeys, peafowl, bantam fowl, and the like.

EXAMPLES

The following examples illustrate various preferred aspects of the invention, but should not be construed as in any way limiting the full scope thereof.

Example 1

Composition of the Product (Per Dose)

| Name of ingredient | Quantity | Function |
|---|---|---|
| Active ingredient(s) | | |
| Inactivated Avian Influenza Virus H5N9 Strain A/CK/Italy/22A/H5N9/1998 | ≧128 HA | active ingredient |
| Inactivated Avian Influenza Virus, H7N1 Strain A/CK/Italy/1067/H7N1/1999 | ≧128 HA | active ingredient |
| Constituents of the adjuvants | | |
| Light Mineral Oil | 230 mg | adjuvant |
| sorbitan sesquioleate (vegetable) | 22.5 mg | emulsifier |
| Polysorbate 80 (vegetable) | 4.3 mg | emulsifier |
| Constituents of the excipients | | |
| Thiomersal | 0.02 mg | preservative |
| Phosphate Buffered Saline | Ad 0.5 ml | diluent |

Development Pharmaceutics

Strains Included in POULVAC® i-AI H5N9, H7N1

The strains, Avian Influenza Virus H5N9 and Avian Influenza virus H7N1, for POULVAC i-AI H5N9, H7N1 were selected based on prevalence in the field. Both strains were supplied by the Instituto Zooprofilattico Sperimentale delle Venezie (IZS), Italy. Their efficacy has been demonstrated by sero conversion of chickens.

Adjuvant Included in POULVAC i-AI H5N9, H7N1

The adjuvant was chosen based on the well-established immunostimulating effect of mineral oil emulsions, formulated as water in oil (W/O) emulsion. A pharmaceutical grade light mineral oil (NF) Drakeoil 5 is used in the formulation.

In order to achieve a stable water-in-oil emulsion (W/O), it is necessary to use surfactants. The surfactants Sorbitan Sesquioleate (vegetable), a hydrophobic surfactant, and Polysorbate 80 (vegetable), a hydrophilic surfactant, were chosen because of their emulsifying properties. The use of a combination of these surfactants has now been shown to result in a stable emulsion.

Arlacel 83V=Sorbitan sesquioleate, an equimolar mixture of monoesters and diesters;

CAS number=8007-43-9. It is used in the preparations of creams, emulsions and ointments.

Tween 80V=Polysorbate 80=Polyoxyethylene 20 sorbitan monooleate;

CAS number=9005-65-6. It is used in the preparation of stable oil-in-water emulsions.

Sorbitan esters like Arlacel 83V produce stable W/O emulsions but are frequently used in combination with varying proportions of a polysorbate like Tween 80V to produce a W/O emulsion.

Both the Arlacel 83V and Tween 80V used to formulate the product are of vegetable origin.

Dose Volume & Vaccination Schedule

The dose volume of 0.5 ml is common for use in the poultry industry.

POULVAC i-AI H5N9, H7N1

Efficacy Based on Serological Studies

1. Exploratory Dose Response Study

An exploratory dose titration study was carried out to determine the antibody response to varying antigen HA levels. Four experimental vaccines containing antigen concentrations of 256, 128, 64 or 32 HA units were prepared and each one was used to intramuscularly vaccinate 10 SPF chickens at two and four weeks of age. A group of ten similar chickens were left unvaccinated as controls. Blood samples were taken prior to each vaccination and two weeks, 6 weeks and 10 weeks after the second vaccination to monitor the serology. Samples of sera were evaluated using a haemagglutination inhibition (HI test) in house and were also evaluated at the Istituto Zooprofilattico Sperimentale (IZS) by HI test.

The serological data showed that all birds were seronegative against the two avian influenza strains prior to vaccination and that all unvaccinated birds remained seronegative throughout the study.

H5N9 Serological Results

Results obtained in our laboratories were generally higher than at the IZS but were within 2-4 dilutions (see Table 1 below). Two weeks after the first vaccination with vaccine containing 128 or 256 HA units all ten vaccinates had a titre of at least 16 HI units (our data) and 4 HI units (IZS). The second dose of vaccine induced a strong anamnestic response to H5N9 in all chickens and two weeks later titres of at least 64 HI units were seen in all birds receiving the higher titred vaccine.

H7N1 Serological Results

Results obtained in our laboratories were again generally higher than at the IZS but the difference of 3-8 fold was greater than for H5N9. In any case, taking the more conservative titres from the IZS results, it is clear that two weeks after the first vaccination all chickens receiving vaccine with 128 or 256 HA units had a titre of at least 8 HI units. The second dose of vaccine induced a very strong anamnestic response to H7N1 in all chickens and two weeks later titres of at least 512 HI units were seen in all birds receiving the higher titred vaccine.

These results indicates that POULVAC i-AI H5N9, H7N1 can induce titres against H5N9 and H7N1 above the level of 1:16 which is considered to be protective by the European Council (Council Directive 92/40/EEC).

TABLE 1

Summary comparison of HI titres between
Fort Dodge Veterinaria S.A. (FD) and in
Istituto Zooprofilattico Sperimentale delle Venezie (IZSV)
HI geometric mean titers

| Antigen concentration | Age in weeks | H5N9 FD | H5N9 IZSV | H7N1 FD | H7N1 IZSV |
|---|---|---|---|---|---|
| 256 HAu for each subtype | 2 w | 1 | 1 | 1 | 1 |
| | 4 w | 59.7 | 27.9 | 274.4 | 52 |
| | 6 w | 1910.8 | 388 | 8780 | 1910.8 |
| | 10 w | 73.5 | PR | 274.4 | PR |
| | 14 w | 26 | PR | 168.9 | PR |
| 128 HAu for each subtype | 2 w | 1 | 1 | 1 | 1 |
| | 4 w | 39.4 | 13 | 274.4 | 32 |
| | 6 w | 831.8 | 256 | 4390 | 831.8 |
| | 10 w | 69.1 | PR | 276.5 | PR |
| | 14 w | 50.8 | PR | 74.7 | PR |
| 64 HAu for each subtype | 2 w | 1 | 1 | 1 | 1 |
| | 4 w | 19.7 | 4.3 | 90.5 | 8 |
| | 6 w | 861 | 207.9 | 2786.9 | 338 |
| | 10 w | 42.2 | PR | 111.4 | PR |
| | 14 w | 34.3 | PR | 64 | PR |
| 32 HAu for each subtype | 2 w | 1 | 1 | 1 | 1 |
| | 4 w | 4.6 | 1.87 | 13 | 2.1 |
| | 6 w | 445.7 | 111.4 | 2048 | 157.6 |
| | 10 w | 34.6 | PR | 52 | PR |
| | 14 w | 27.4 | PR | 47 | PR |
| Unvaccinated | 2 w | 1 | 1 | 1 | 1 |
| | 4 w | 1 | 1 | 1 | 1 |
| | 6 w | 1 | 1 | 1 | 1 |
| | 10 w | 1 | PR | 1 | PR |
| | 14 w | 1 | PR | 1 | PR |

FD: HI TITERS OBTAINED IN FORT DODGE VETERINARIA S.A.
IZSV: HI TITERS OBTAINED IN ISTITUTO ZOOPROFILATTICO SPERIMENTALE DELLE VENEZIE
2 W: AGE AT FIRST VACCINATION AND BLEEDING
4 W: AGE AT SECOND VACCINATION AND BLEEDING
6 W: TWO WEEKS, 6 WEEKS, 10 WEEKS OR 14 WEEKS AFTER SECOND VACCINATION AND BLEEDING
PR: Pending results
For calculation purposes, if a serum had no titer, it was considered that it had a titer 1

PR: Pending Results

For calculation purposes, if a serum had no titer, it was considered that it had a titer 1

2. Efficacy Study

The efficacy of POULVAC i-AI H5N9, H7N1 in chickens has been evaluated by the following procedure.

110-A1-E-14-04. Twenty SPF chickens were vaccinated intramuscularly at two weeks of age with a single dose of 0.5 ml formulated at minimum titre (128 HA units) for both antigens. A second dose of vaccine was given 3 weeks later when the birds were 5 weeks of age. Twenty similar chickens were kept as unvaccinated controls for comparison. Blood samples were taken prior to each vaccination and three weeks after the second vaccination to monitor the serology. Samples of sera were evaluated using a haemagglutination inhibition (HI test) in-house and were also evaluated at the Istituto Zooprofilattico Sperimentale (IZS) by HI test.

The serological data showed that all birds were seronegative against the two avian influenza strains prior to vaccination and that all unvaccinated birds remained seronegative throughout the study.

H5N9 Serological Results

Results obtained at our laboratories were generally higher than at the IZS but were within 2-4 dilutions (see table 2 below). Three weeks after the first vaccination all twenty vaccinates had a titre of at least 128 HA units (our data) and 64 HA units (IZS). This indicates that a single dose of POULVAC i-AI H5N9, H7N1 can induce titres against H5N9 above the level of 1:16, which is considered to be protective by the European Council (Council Directive 92/40/EEC).

The second dose of vaccine induced a strong anamnestic response to H5N9 in all chickens and is again indicative that good protection will be seen against challenge.

H7N1 Serological Results

Results obtained at our laboratories were again generally higher than at the IZS but the difference of 3-8 fold was greater than for H5N9. It is not yet known why this difference in testing is so wide. In any case, taking the more conservative titres from the IZS results, it is clear that three weeks after the first vaccination all twenty vaccinates had a titre of at least 128 HA units. This indicates that a single dose of POULVAC i-AI H5N9, H7N1 can induce titres against H7N1 significantly above the level of 1:16 which is considered to be protective by the European Council (Council Directive 92/40/EEC).

The second dose of vaccine induced a very strong anamnestic response to H7N1 in all chickens and is again indicative that good protection will be seen against challenge.

TABLE 2

Summary comparison of HI titres between Fort Dodge Veterinaria S.A. (FD) and in Istituto Zooprofilattico Sperimentale delle Venezie (IZSV) HI expressed as geometric mean titers

| Antigen concentration | Age in weeks | Avian Influenza subtypes | | | |
|---|---|---|---|---|---|
| | | H5N9 | | H7N1 | |
| | | FD | IZSV | FD | IZSV |
| Group 1 Vaccinates | 2 w | 1 | 1 | 1 | 1 |
| | 5 w | 374.8 | 163.1 | 955.4 | 304.4 |
| | 8 w | 1351.2 | 588.1 | 14263.1 | 1782.9 |
| Group 2 Controls | 2 w | 1 | 1 | 1 | 1 |
| | 5 w | 1 | 1 | 1 | 1 |
| | 8 w | 1 | 1 | 1 | 1 |

For calculation purposes, if a serum had no titer, it was considered that it had a titer 1.

Comparative Example 2

For this example, reference is made to two published texts: Reference 1: Capua et al., Developments of a DIVA (Differentiating Infected from Vaccinated Animals) Strategy Using a Vaccine Containing a Herterologous Neuraminidase for the Control of Avian Influenza; Avian Pathology 32, 47-55 (2003); and Reference 2: Ellis et al., Vacination of Chickens Against H5N1 Avian Influenza in the Face of an Outbreak Interrupts Virus Transmission. Reference 1 notes that birds vaccinated with 2 doses of a competitor's vaccine H7N3 at age 2 and 4 weeks had serology at 6 weeks with a geometric mean titre of 45 as measured by HI, with 11 out of 13 birds achieving titres greater than 1:16 HI (deemed to be protective). Birds vaccinated once at 3 weeks of age with serology taken at week 6 showed a geometric titre of 19 as measured by HI. In this case, only 8 out of 13 birds achieved HI titres greater than 1:16. In contrast, the H7N1 fraction results described herein are considerably higher than this on both a single and double dose program. Reference 2 notes birds vaccinated with 1 dose of another competitor's influenza vaccine in birds ranging from 56-99 days old. 15 days post vaccination, the geometric mean titre was 11.7 as measured by HI, with 32 out of 60 birds showing an HI titre of 1:16 or greater. 22 days post vaccination, the geometric mean titre was 33.9, as measured by HI, with 49 out of 60 birds showing HI titres of 1:16 or greater. The results obtained herein, however, seem to demonstrate greater efficacy.

Example 3

Poulvac XXX Efficacy Trial for Prophylactic Vaccination in Turkeys

Summary of results—This trial was performed at the Istituto Zooprofilattico Sperimentale delle Venezie, Padova, Italy which is OIE and National Reference Laboratory for AI and ND. The trial was based on previous work but was developed to test the efficay of Poulvac XXX as a tool for prophylactic vaccination against re-emergence of a highly adapted virus (A/Ty/Italy/8000/H7N3/2002). There was introduction of a novel strain with a low degree of adaptation to the domestic host (A/ty/ltaly/H5N2/1980). The trial was performed in chickens and turkeys with different infectious doses Experimental Trial Turkeys were Vaccinated with Poulvac XXX, 0.5 ml/sc at 8, 34, 60 days of age. There were 4 experimental groups, 2 vaccinated and 2 unvaccinated, challenged 21 days after third vaccination with $10^4$EID/50 in 100 ul/intranasally. (LPAI A/ty/Italy/8000/2002/H7N3 LPAI A/ty/ltaly/H5N2/1980). There was one group of unvaccinated controls. Shedding (tracheal and cloacal swabs collected on days 3, 5, 7, 10, 14, 20), serology and clinical signs were evaluated.

METHODS—Virus isolation was done according to EU Directive 92/40/EC. Haemagglutination inhibition test was done according to EU Directive 92/40/EC. Realtime RT-PCR was done according to Cattoli et al., (2004), Avian Pathology, 33(4), pp. 432-437. Anti N antibody detection test "DIVA" test according to Capua et al., (2003) Avian Pathology 32 (1), 47-55.

DEFINITIONS AND STATISTICAL TESTS—Infection: combination of virological positivity by RRT-PCR (tracheal or cloacal) AND seroconversion and positivity to "DIVA" test. Seroconversion: increase of at least 4 logs (pre and post-challenge titer). Comparison of shedding between vaccinated and unvaccinated groups: Fisher's exact P. Comparison of pre and post challenge titers: Nonparametric sign test (pre-post within the same group) and Wilcoxon (Mann-Whitney) two samples test (comparison between the increase in titer among different groups, ie to establish whether there is a difference in increase in titer between vaccinated group and unvaccinated group following challenge).

Results

Turkeys H5N2 $10^4$EID/50 CHALLENGE

1. Comparison Between the Indicators of Achievement of Infection Between Vaccinated Vs Unvaccinated Birds Fisher's Exact P=0.0005 (<0.01)

Significant: There is a statistically significant difference between the number of birds in which infection was achieved in vaccinated versus unvaccinated birds

| | Positive | Negative | Total |
|---|---|---|---|
| Vaccinated | 1 | 9 | 10 |
| Unvaccinated | 9 | 1 | 10 |

2. Comparison Between Shedding Levels (Cloacal and Tracheal Swabs) in Vaccinated vs Unvaccinated Birds Fisher's Exact P=0.0005 (<0.01)

Significant: in vaccinated birds shedding levels were significantly lower than unvaccinated birds

|  | Positive | Negative | Total |
|---|---|---|---|
| Vaccinated | 44 | 96 | 140 |
| Unvaccinated | 57 | 69 | 126 |

3. Comparison between HI Titer Pre and Post Challenge in Vaccinated vs Unvaccinated Birds Nonparametric Sign Test Unvaccinated: H5N2: P=0.0039 (<0.01); H5N9: P=0.0039 (<0.01)

Vaccinated: H5N2: P=0.1797 (>0.05); H5N9: P=0.0039 (<0.01)

Significant: in vaccinated birds the rise in serologic titer to the challenge virus is not significant. In the unvaccinated birds instead there was a significant rise in titer.

|  | Prechallenge H5N2 | Postchallenge H5N2 | Prechallenge H5N9 | Postchallenge H5N9 |
|---|---|---|---|---|
| Vaccinated | 7.2* | 9.6 | 6.0 | 6.9 |
| Unvaccinated | 0 | 8.5 | 0 | 6.2 |

*log 2

Turkeys H7N3 $10^4$EID/50 Challenge

1. Comparison Between the Indicators of Achievement of Infection Between Vaccinated Vs Unvaccinated Birds Fisher's Exact P=0.0001 (<0.01)

Significant: There is a statistically significant difference between the achievement of infection in vaccinated versus unvaccinated birds

|  | Positive | Negative | Total |
|---|---|---|---|
| Vaccinated | 1 | 9 | 10 |
| Unvaccinated | 9 | 1 | 10 |

2. Comparison Between Shedding Levels (Cloacal and Tracheal Swabs) in Vaccinated vs Unvaccinated Birds Fisher's Exact P=0.0000 (<0.01)

Significant: in vaccinated birds shedding levels were significantly lower than unvaccinated birds

|  | Positive | Negative | Total |
|---|---|---|---|
| Vaccinated | 21 | 119 | 140 |
| Unvaccinated | 63 | 63 | 126 |

3. Comparison Between HI Titer Pre and Post Challenge in Vaccinated vs Unvaccinated Birds Nonparametric Sign Test Unvaccinated: H7N1: P=0.0039 (<0.01); H7N3: P=0.0039 (<0.01)

Vaccinated: H7N1: P=0.0020 (<0.01); H7N3: P=0.0215 (<0.05)

Non Significant: in vaccinated birds there was a significant rise in serologic titer to the challenge virus comparable to the one observed in the unvaccinated birds.

|  | Prechallenge H7N1 | Postchallenge H7N1° | Prechallenge H7N3 | Postchallenge H7N3 |
|---|---|---|---|---|
| Vaccinated | 8.4* | 10.6 | 5.3 | 7.1 |
| Unvaccinated | 0 | 9 | 0 | 6.8 |

*log 2
°The higher serologic reactivity with the H7N1 virus is to be attributed to the particular strain of virus. In order to assess significance the tier of the challenge virus must be considered.

CONCLUSIONS—Turkeys—Poulvac XXX in a 3 shot program is able to significantly reduce number of infected birds, shedding and clinical signs with a $10^4$ EID/50 challenge of an H7N3 strain endemic to the Italian turkey population. It is also able to significantly reduce the number of infected birds and shedding with $10^4$ EID/50 challenge of an H5N2 strain selected to mimic a novel introduction. Prophylactic vaccination in turkeys has resulted in a lower susceptibility of the group to experimental infection and in significantly lower shedding levels.

Example 4

Poulvac XXX efficacy trial for prophylactic vaccination in chickens Summary of results—The study was performed at the Istituto Zooprofilattico Sperimentale delle Venezie, Padova, Italy which is OIE and National Reference Laboratory for AI and ND. The trial was based on previous work but was developed to test the efficay of Poulvac XXX as a tool for prophylactic vaccination against: re-emergence of a highly adapted virus (A/Ty/ltaly/8000/H7N3/2002). There was introduction of a novel strain with a low degree of adaptation to the domestic host (A/ty/ltaly/H5N2/1980). The trial was performed in chickens and turkeys with different infectious doses.

EXPERIMENTAL TRIAL—Chickens were vaccinated with Poulvac XXX, 0.5 ml/im at 2 and 5 weeks of age. There were 4 experimental groups, 2 vaccinated and 2 unvaccinated challenged 21 days after second vaccination with $10^6$ EID/50 in 100 ul/intranasally. (LPAI A/ty/Italy/8000/2002/H7N3 LPAI A/ty/ltaly/H5N2/1980). There was one group of unvaccinated controls. Shedding (tracheal and cloacal swabs collected on days 3, 5, 7, 10, 14, 20), serology and clinical signs were evaluated.

METHODS—Virus isolation was done according to EU Directive 92/40/EC. The Haemagglutination inhibition test was done according to EU Directive 92/40/EC. Realtime RT-PCR was done according to Cattoli et al., (2004), Avian Pathology, 33(4), pp. 432-437. Anti N antibody detection test "DIVA" test was done according to Capua et al., (2003) Avian Pathology 32 (1), 47-55.

Definitions and statistical tests—Infection: combination of virological positivity by RRT-PCR (tracheal or cloacal) AND seroconversion and positivity to "DIVA" test. Seroconversion: increase of at least 4 logs (pre and post-challenge titer). Comparison of shedding between vaccinated and unvaccinated groups: Fisher's exact P. Comparison of pre and post challenge titers: Nonparametric sign test (pre-post within the same group) and Wilcoxon (Mann-Whitney) two samples test (comparison between the increase in titer among different groups, ie to establish whether there is a difference in increase in titer between vaccinated group and unvaccinated group following challenge).

Results

Chickens H5N2 $10^6$EID/50 Challenge

1. Comparison Between the Indicators of Achievement of Infection Between Vaccinated Vs Unvaccinated Birds Fisher's Exact P=0.0433 (<0.05)

Significant: in vaccinated birds infection was not achieved

|  | Positive | Negative | Total |
| --- | --- | --- | --- |
| Vaccinated | 0 | 10 | 10 |
| Unvaccinated | 4 | 6 | 10 |

2. Comparison Between Shedding Levels (Cloacal and Tracheal Swabs) in Vaccinated Vs Unvaccinated Birds Fisher's Exact P=0.0008 (<0.01)

Significant: in vaccinated birds shedding levels were significantly lower than unvaccinated birds—(because infection was not achieved)

|  | Positive | Negative | Total |
| --- | --- | --- | --- |
| Vaccinated | 0 | 140 | 140 |
| Unvaccinated | 10 | 130 | 140 |

3. Comparison Between HI Titer Pre and Post Challenge in Vaccinated Vs Unvaccinated Birds Nonparametric Sign Test Unvaccinated: H5N2: P=0.0078 (<0.01); H5N9: P=0.0078 (<0.01)

Vaccinated: H5N2: P=0.4531 (>0.05); H5N9: P=0.6875 (>0.05)

Significant: in vaccinated birds the rise in serologic titer to the challenge virus is not significant (because infection was not achieved). In the unvaccinated birds instead there was a significant rise in titer.

|  | Prechallenge H5N2 | Postchallenge H5N2 | Prechallenge H5N9 | Postchallenge H5N9 |
| --- | --- | --- | --- | --- |
| Vaccinated | 8.9* | 9.6 | 7.7 | 8.5 |
| Unvaccinated | 0 | 4.1 | 0 | 4.1 |

*log 2

Chickens H7N3 $10^6$EID/50 Challenge

1. Comparison Between the Indicators of Achievement of Infection Between Vaccinated Vs Unvaccinated Birds Fisher's Exact P=0.0015 (<0.01)

|  | Positive | Negative | Total |
| --- | --- | --- | --- |
| Vaccinated | 0 | 10 | 10 |
| Unvaccinated | 7 | 3 | 10 |

2. Comparison Between Shedding Levels (Cloacal and Tracheal Swabs) in Vaccinated Vs Unvaccinated Birds Fisher's Exact P=0.0000 (<0.01)

Significant: in vaccinated birds shedding levels were significantly lower than unvaccinated birds—(because infection was not achieved)

|  | Positive | Negative | Total |
| --- | --- | --- | --- |
| Vaccinated | 2 | 138 | 140 |
| Unvaccinated | 25 | 115 | 140 |

3. Comparison Between HI Titer Pre and Post Challenge in Vaccinated Vs Unvaccinated Birds Nonparametric Sign Test Unvaccinated: H7N1: P=0.0020 (<0.01); H7N3: P=0.0020 (<0.01)

Vaccinated: H7N1: P=0.0020 (<0.01); H7N3: P=1.0000 (>0.05)

Significant: in vaccinated birds there was not a significant rise in serologic titer to the challenge virus (because infection was not achieved). In the unvaccinated birds instead there was a significant rise in titer.

|  | Prechallenge H7N1 | Postchallenge H7N1° | Prechallenge H7N3 | Postchallenge H7N3 |
|---|---|---|---|---|
| Vaccinated | 8.4* | 10.8 | 6.1 | 6.1 |
| Unvaccinated | 0 | 5 | 0 | 3.5 |

*log 2
°The higher serologic reactivity with the H7N1 virus is to be attributed to the particular strain of virus. In order to assess significance the tier of the challenge virus must be considered.

CONCLUSIONS—Chickens. Poulvac XXX in a 2 shot program is able to Prevent infection with $10^6$ EID/50 of an H7N3 strain endemic to the Italian turkey population. It is also able to prevent infection with 106 EID/50 of an H5N2 strain selected to mimic a novel introduction. Prophylactic vaccination in chickens has prevented the establishment of active infection in chickens.

While the invention has been described in each of its various embodiments, it is expected that certain modifications thereto may be undertaken and effected by the person skilled in the art without departing from the true spirit and scope of the invention, as set forth in the previous description and as further embodied in the following claims.

What is claimed is:

1. A vaccine composition which is effective in preventing or ameliorating Avian Influenza Virus infection, which comprises at least two inactivated strains of avian influenza virus, wherein the combined hemagglutinin (HA) total is at least about 200 HA units/dose of said vaccine composition, and wherein each of said strains presents at least about 128 HA units/dose, and further wherein at least one of said strains is an H5N9 avian influenza virus, and wherein at least one of said strains is an H7N1 avian influenza strain.

2. The vaccine composition of claim 1, further comprising a pharmacologically acceptable carrier.

3. The vaccine composition of claim 2, further comprising at least one additional poultry antigen.

4. The vaccine composition of claim 3, wherein said carrier is at least one member selected from the group consisting of aqueous carriers and emulsions.

5. The vaccine composition of claim 4, wherein said carrier is a water-in-oil emulsion.

6. The vaccine composition of claim 5, wherein said emulsion comprises at least two surfactants.

7. The vaccine composition of claim 6, wherein said surfactants are selected from the group consisting of sorbitan oleate esters and ethylene oxide/propylene oxide block copolymers.

8. The vaccine composition of claim 7, wherein said emulsion comprises at least two sorbitan oleate esters.

9. The vaccine composition of claim 8, wherein said esters are TWEEN® 80 and sorbitan sesquioleate ester.

10. A method of preventing or ameliorating an outbreak of Avian Influenza virus infection, which comprises administering to a poultry member a vaccine composition which comprises at least two inactivated strains of avian influenza virus, wherein the combined hemagglutinin (HA) total is at least about 200 HA units/dose of said vaccine composition, and wherein each of said strains presents at least about 128 HA units/dose, and further wherein at least one of said strains is an H5N9 avian influenza virus, and wherein at least one of said strains is an H7N1 avian influenza strain.

11. The method of claim 10, wherein said vaccine composition is administered via drinking water or spraying.

12. The method of claim 10, wherein said dose is within the range of about 0.25 mL to 2.0 mL per poultry member.

13. The method of claim 12, wherein said vaccine is administered in no more than one dose.

14. A vaccine composition which is effective in preventing or ameliorating Avian Influenza Virus infection, which comprises at least two inactivated strains of avian influenza virus, wherein the combined hemagglutinin (HA) total is at least about 250 HA units/dose of said vaccine composition, and wherein each of said strains presents at least about 150 HA units/dose, and further wherein at least one of said strains is an H5N9 avian influenza virus, and wherein at least one of said strains is an H7N1 avian influenza strain, and also wherein said composition contains two surfactants consisting essentially of sorbitan oleate esters.

15. The composition of claim 14, wherein said surfactants are TWEEN® 80 and sorbitan sesquioleate ester.

16. The composition of claim 14, wherein each of said strains presents about 192 HA units/dose.

17. The composition of claim 14, wherein the combined HA total is at least about 300 HA units/dose.

* * * * *